(12) United States Patent
Luther et al.

(10) Patent No.: US 6,235,271 B1
(45) Date of Patent: *May 22, 2001

(54) UV-PROTECTION FORMULATION

(75) Inventors: Helmut Luther, Grenzach-Wyhlen (DE); Albert Stehlin, Rosenau (FR); Bernd Herzog, Grenzach-Wyhlen (DE)

(73) Assignee: Ciba Specialty Chemicals Corporation, Tarrytown, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/122,554

(22) Filed: Jul. 24, 1998

(30) Foreign Application Priority Data

Jul. 26, 1997 (GB) .................................. 9715751

(51) Int. Cl.⁷ ............................. A61K 7/42; A61K 7/44; A61K 7/00; A61K 9/14
(52) U.S. Cl. ............................. 424/59; 424/60; 424/401; 424/487; 514/937
(58) Field of Search ............................. 424/401, 59, 60, 424/487; 514/937

(56) References Cited

U.S. PATENT DOCUMENTS

| | | | |
|---|---|---|---|
| 4,617,390 | * 10/1986 | Hoppe et al. | 544/197 |
| 4,804,531 | * 2/1989 | Grollier | 424/47 |
| 5,252,323 | * 10/1993 | Richard et al. | 424/59 |
| 5,332,568 | 7/1994 | Raspanti | 424/59 |
| 5,338,539 | 8/1994 | Raspanti | 424/59 |
| 5,362,481 | 11/1994 | Raspanti | 424/59 |
| 5,518,713 | 5/1996 | Raspanti | 424/59 |
| 5,520,906 | 5/1996 | Stein et al. | 424/59 |
| 5,601,811 | 2/1997 | Gallagher et al. | 424/709 |
| 5,618,520 | 4/1997 | Hansenne et al. | 424/59 |
| 5,629,365 | * 5/1997 | Razavi | 524/37 |
| 5,788,952 | 8/1998 | Gers-Barlag et al. | 424/59 |

FOREIGN PATENT DOCUMENTS

| | | |
|---|---|---|
| 0517104 | 12/1992 | (EP) . |
| 0570838 | 11/1993 | (EP) . |
| 0709080 | 5/1996 | (EP) . |
| 0 761 201 | * 3/1997 | (EP) . |
| 0761201 | 3/1997 | (EP) . |
| 0775698 | 5/1997 | (EP) . |
| 0780382 | 6/1997 | (EP) . |
| 2286774 | 8/1995 | (GB) . |
| 2 286 774 | * 8/1995 | (GB) . |
| 2303549 | 2/1997 | (GB) . |
| 2 303 549 | * 2/1997 | (GB) . |
| 97/00851 | 1/1997 | (WO) . |
| 97/03642 | 2/1997 | (WO) . |

OTHER PUBLICATIONS

"Redox Mechanisms in Heterogeneous Photocatalysis. The Case of Holes versus OH• Radical Oxidation and Free Versus Surface Bound OH• Radical Oxidation Processes", Serpone et al., Electrochemistry in Colloids and Dispersions (1992), pp. 399–416.

Diffey et al., J. Soc. Cosmet. Chem., 40, pp. 127–133, (May/Jun. 1989).

Klein, Cosmetics & Toiletries/45, vol. 107, Oct. 1992, Encyclopedia of UV Absorbers for Sunscreen Products.

Lowe, N.G. et al., Sunscreens: Development, Evaluation, and Regulatory Aspects, M. Dekker Inc., New York & Basle (1990).

Derwent Abstr. 97–054365/06 for EP 748624; 12/96.
Derwent Abstr. 97–101592/10 for EP 755670; 01/97.

* cited by examiner

*Primary Examiner*—Shelley A. Dodson
*Assistant Examiner*—Manna Lamm
(74) *Attorney, Agent, or Firm*—Kevin T. Mansfield

(57) ABSTRACT

The present invention provides, as a first aspect, a sun protection agent, which is especially suitable for use in pharmaceutical or cosmetic applications, comprising a) a micronized organic UV absorber; and one, or preferably both of;

b) an oil-soluble, non-micronized UV absorber and/or an inorganic micropigment; and c) a polymeric hollow sphere additive and/or a polymer selected from xanthan and/or polyvinylpyrrolidone.

The present invention also provides a sunscreen composition comprising A) 0.1 to 15%, preferably 0.5 to 10% by weight, based on the total composition of a sun screen agent according to the present invention; and B) a cosmetically acceptable carrier.

24 Claims, No Drawings

UV-PROTECTION FORMULATION

The present invention relates to new formulations and, in particular, to new UV-protection formulations which comprise a combination of a micronised UV absorber and one, or preferably both of i) an oil-soluble, non-micronised UV absorber and/or an inorganic micropigment and ii) a polymeric hollow sphere additive and/or a polymer selected from xanthan and/or polyvinylpyrrolidone. The new combinations exhibit an unexpected synergistic sun protection effect. This synergistic effect is greatly enhanced when the micronised UV absorber and the oil-soluble, non-micronised UV absorber and/or an inorganic micropigment are used in combination with a polymeric hollow sphere additive and/or a polymer selected from xanthan and/or polyvinylpyrrolidone.

It has long been known that prolonged exposure to UV radiation which reaches the surface of the earth can lead to the formation of erythemas or light dermatoses, as well as to an increased incidence of skin cancers, or accelerated skin ageing.

Various sunscreen formulations have been proposed which include a material which is intended to counteract UV radiation, thereby inhibiting the said undesired effects on the skin.

A great number of compounds has been proposed for use as UV protectants in sunscreen formulations, especially soluble organic UV absorbers and insoluble micronised inorganic compounds, in particular zinc oxide and titanium dioxide.

With respect to the use in sunscreen formulations of soluble organic UV absorbers, they have the disadvantages that their effectiveness as UV protectants in terms of SPF (Sun Protection Factor) in a sunscreen formulation is often too low for commercial purposes; as a result of their solubility, they exhibit relatively high allergenic potential; and that as a result of intrinsic photochemical lability, the duration of the protective effect is often too low.

The high specific weight of insoluble inorganic compounds, such as titanium dioxide leads to a reduced stability of formulations containing them. Moreover, such inorganic compounds have been claimed to generate toxic radicals under the influence of light and water ("Redox Mechanisms in Heterogeneous Photocatalysis", Serpone et al, Electrochemistry in Colloids and Dispersions, Editors Mackay and Texter, VCH Publishers Inc., New York 1992).

In GB-A-2303549, there is described a method of producing micronised, insoluble organic UV absorbers, as well as a sunscreen composition comprising a) 0.1 to 15%, preferably 0.5 to 10% by weight, based on the total composition of a micronised formulation of an insoluble organic UV absorber, produced according to the said method; and optionally b) a cosmetically acceptable carrier. Micronised, insoluble organic UV absorbers so obtained, when used in sunscreen formulations, provide excellent UV protection and have at least as high an SPF rating as corresponding sunscreen formulations containing a known inorganic UV absorber. Unlike the latter UV absorbers, micronised, insoluble organic UV absorbers show no tendency, under the influence of light, to generate radicals which could damage or sensitise human skin.

In a further development of the concept disclosed in GB-A-2303549, it has now been found that when a micronised organic UV absorber is used in combination with one, or preferably both of i) an oil-soluble, non-micronised UV absorber and/or an inorganic micropigment and ii) a polymeric hollow sphere additive and/or a polymer selected from xanthan and/or polyvinylpyrrolidone, this combination exhibits an unexpected synergistic sun protection effect. This synergistic effect is greatly enhanced when the micronised UV absorber, or the soluble, non-micronised UV absorber are used individually, or preferably in combination together, with a polymeric hollow sphere additive.

Accordingly, the present invention provides, as a first aspect, a sun protection agent, which is especially suitable for use in pharmaceutical or cosmetic applications, comprising
a) a micronised organic UV absorber; and one, or preferably both of;
b) an oil-soluble, non-micronised UV absorber and/or an inorganic micropigment; and
c) a polymeric hollow sphere additive and/or a polymer selected from xanthan and/or polyvinylpyrrolidone.

The relative proportions of components a):b) and/or c) preferably range from 20:80 to 80:20, especially from 40:60 to 60:40, by weight.

The micronised organic UV absorber, component a), is preferably produced by the method described in GB-A-2303549, namely by a process which comprises grinding an organic UV absorber, in coarse particle form, in a grinding apparatus, in the presence of 1 to 50%, preferably 5 to 40% by weight, based on the micronised organic UV absorber, of an alkyl polyglucoside having the formula $C_nH_{2n+1}O(C_6H_{10}O_5)_xH$, in which n is an integer ranging from 8 to 16 and x is the mean polymerisation level of the glucoside moiety ($C_6H_{10}O_5$) and ranges from 1.4 to 1.6, or an ester thereof.

The grinding apparatus used to produce the micronised organic UV absorber may be, e.g., a jet, ball, vibration or hammer mill, preferably a high speed stirring mill or impact mill, especially a rotating ball mill, vibrating mill, tube mill or rod mill.

The alkyl polyglucoside may consist of a $C_1$–$C_{12}$ ester of the compound of formula $C_nH_{2n+1}O(C_6H_{10}O_5)_xH$, namely an ester formed by reacting a $C_1$–$C_{12}$ acid, such formic, acetic, propionic, butyric, sulfosuccinic, citric or tartaric acid, with one or more free OH groups on the glucoside moiety ($C_6H_{10}O_5$).

The micronised organic UV absorber may be, e.g., a triazine, a benzotriazole, a vinyl group-containing amide, a cinnamic acid amide or a sulfonated benzimidazole UV absorber.

A preferred class of triazine compounds is that having the formula

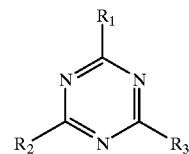

(1)

in which $R_1$, $R_2$ and $R_3$, independently, are H, OH, $C_1$–$C_3$alkoxy, $NH_2$, NH—$R_4$ or $N(R_4)_2$ in which $R_4$ is $C_1$–$C_3$ alkyl, $OR_4$ in which $R_4$ has its previous significance, phenyl, phenoxy or anilino, or pyrrolo, in which the respective phenyl, phenoxy or anilino, or pyrrolo moieties are optionally substituted by one, two or three substitutents selected from OH, carboxy, CO—$NH_2$, $C_1$–$C_3$alkyl or -alkoxy, $C_2$–$C_4$carboxyalkyl, $C_5$–$C_8$cycloalkyl, a methylidenecamphor group, a group —(CH=CH)$_m$C(=O)—$OR_4$ in which m is 0 or 1 and $R_4$ has its previous significance, or a group

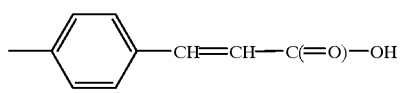
or the corresponding alkali metal, ammonium, mono-, di- or tri-$C_1$–$C_4$alkylammonium, mono-, di- or tri-$C_2$–$C_4$alkanolammonium salts, or the $C_1$–$C_3$alkyl esters thereof.
Preferred compounds of formula (1) are those having one of the formulae
(2)
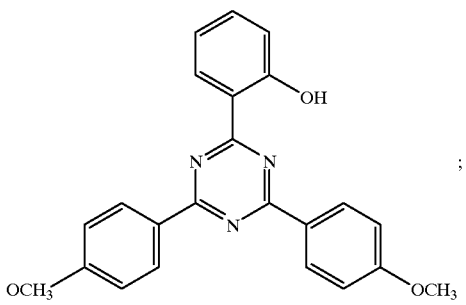
(3)
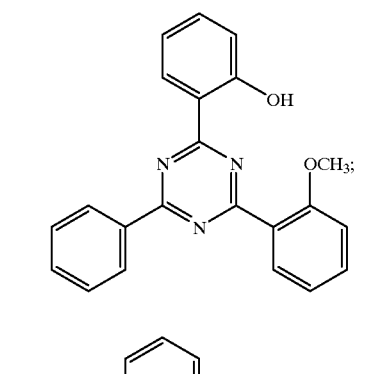
(4)
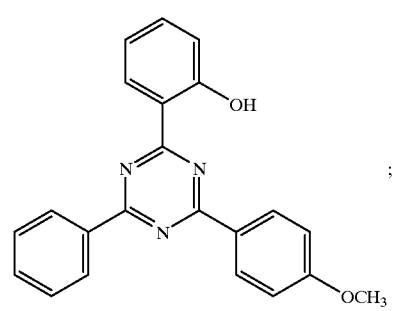
(5)
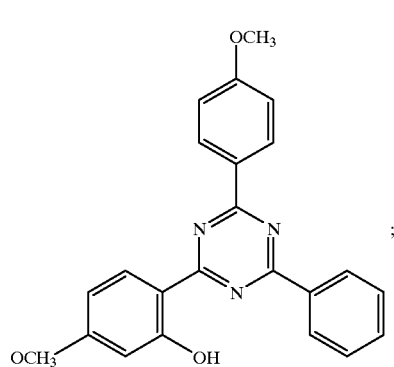
(6)
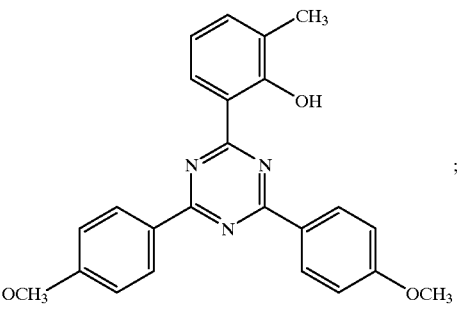
(7)
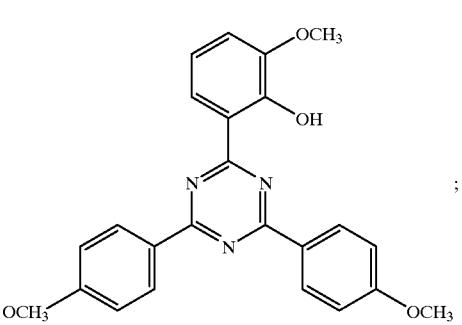
(8)
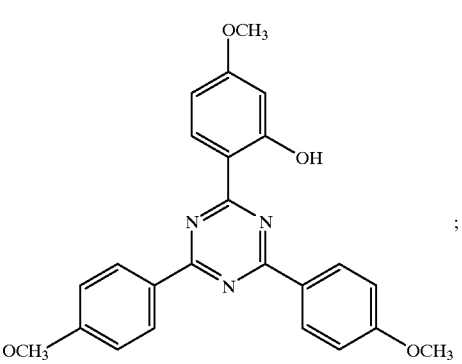
(9)
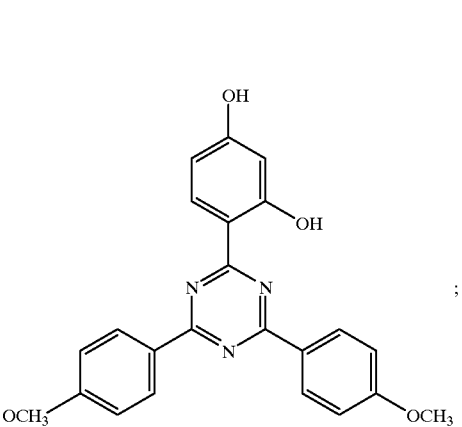

-continued
(10)
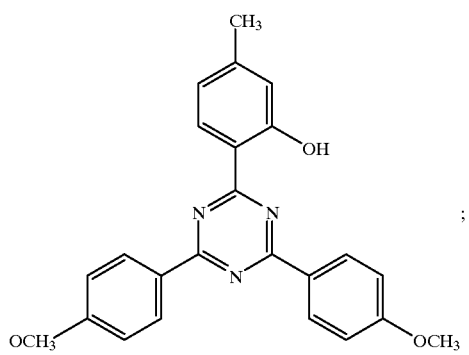
(11)
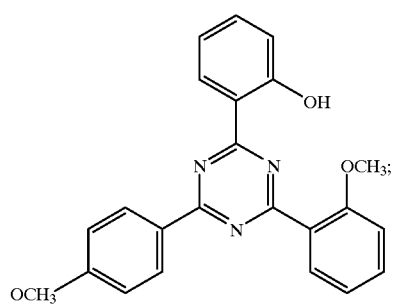
(12)
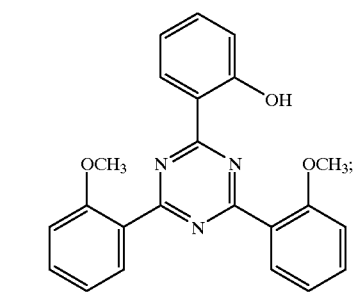
(13)
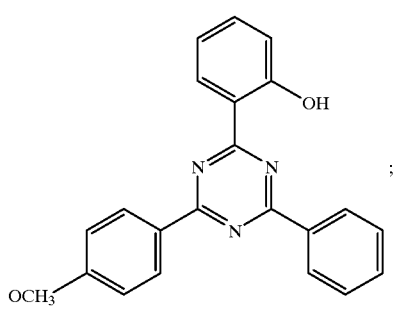
-continued
(14)
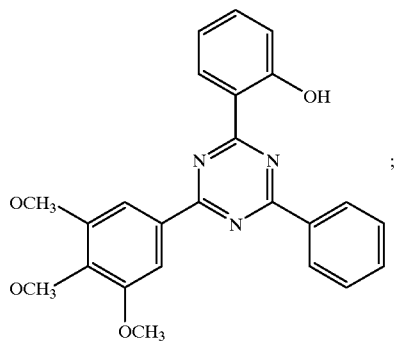
(15)
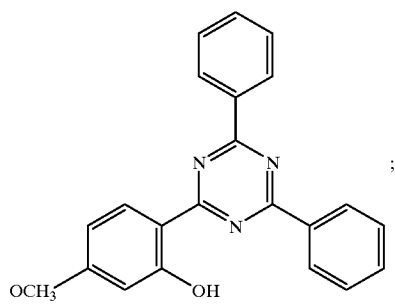
(16)
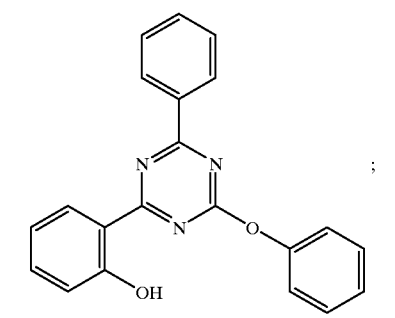
(17)
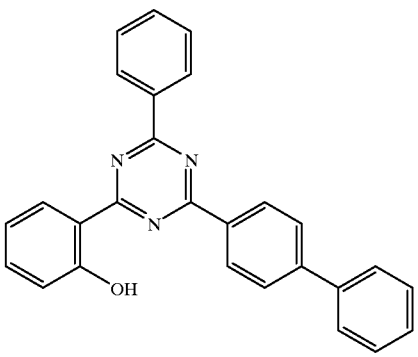

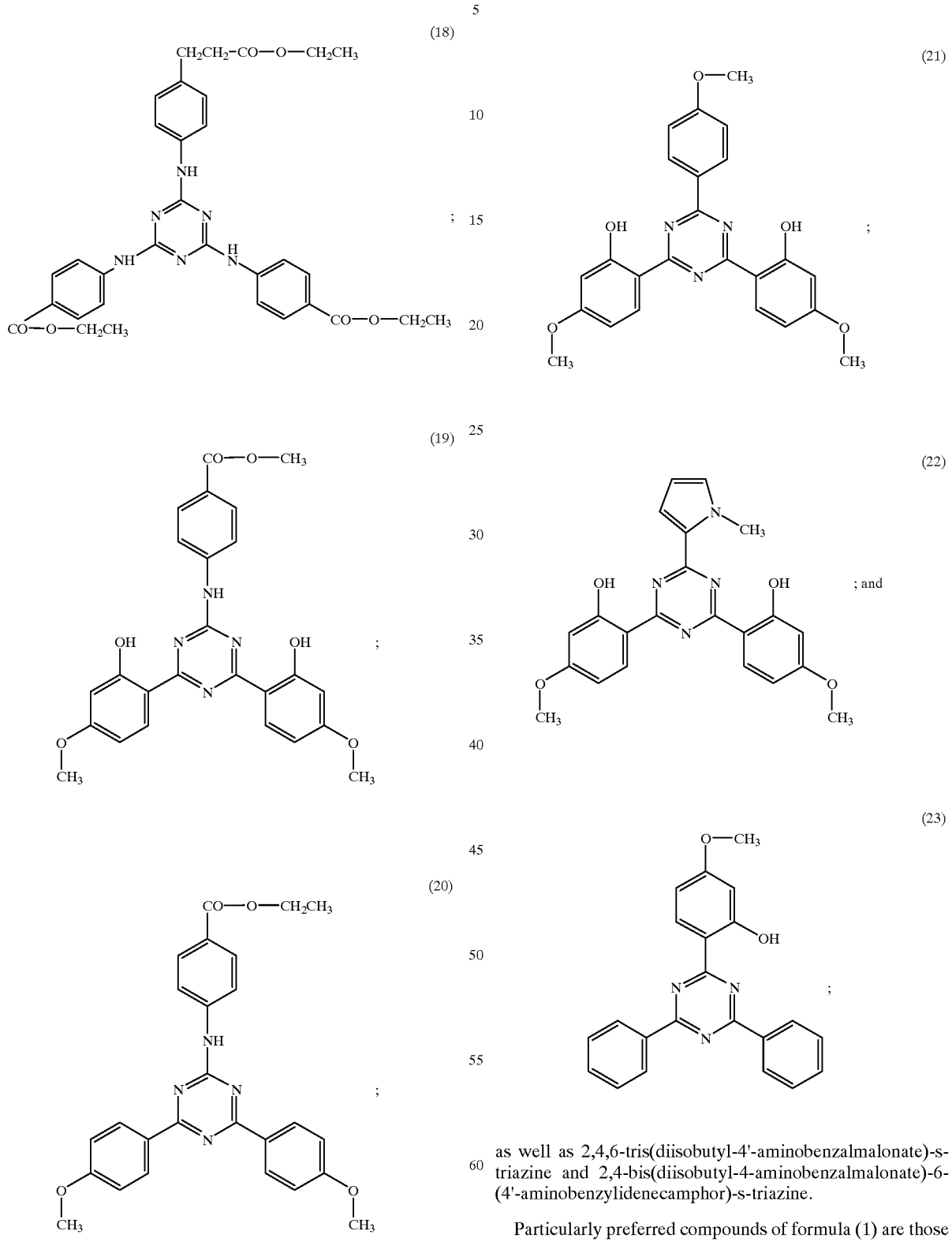
as well as 2,4,6-tris(diisobutyl-4'-aminobenzalmalonate)-s-triazine and 2,4-bis(diisobutyl-4-aminobenzalmalonate)-6-(4'-aminobenzylidenecamphor)-s-triazine.
Particularly preferred compounds of formula (1) are those having the formula (24)

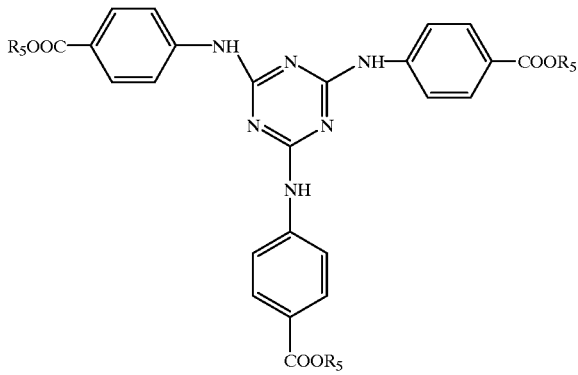

in which the individual radicals $R_5$ are the same or different and each is hydrogen; an alkali metal; an ammonium group $N(R_6)_4$ in which $R_6$ is hydrogen or an organic radical; $C_1$–$C_3$alkyl; or a polyoxyethylene radical which contains from 1 to 10 ethylene oxide units and the terminal OH group of which may be etherified by a $C_1$–$C_3$alcohol.

In relation to the compounds of formula (24), when $R_5$ is an alkali metal it is preferably potassium or, especially sodium; when $R_5$ is a group $N(R_6)_4$ in which $R_6$ has its previous significance, it is preferably a mono-, di- or tri-$C_1$–$C_4$alkylammonium salt, a mono-, di- or tri-$C_2$–$C_4$alkanolammonium salt or a $C_1$–$C_3$alkyl ester thereof; when $R_6$ is a $C_1$–$C_3$alkyl group, it is preferably a $C_1$–$C_2$alkyl group, more preferably a methyl group; and when $R_6$ is polyoxyethylene group, this preferably contains from 2–6 ethylene oxide units.

One preferred class of triazole micronised organic UV absorbers is that having the formula (25)

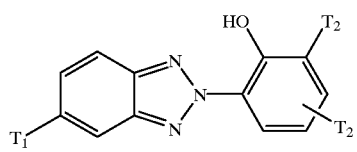

in which $T_1$ is $C_1$–$C_3$alkyl or, preferably, hydrogen; and $T_2$ is $C_1$–$C_4$alkyl, preferably t-butyl, or $C_1$–$C_4$alkyl substituted by phenyl, preferably α,α-dimethylbenzyl.

A further preferred class of triazole micronised organic UV absorbers is that having the formula (26)

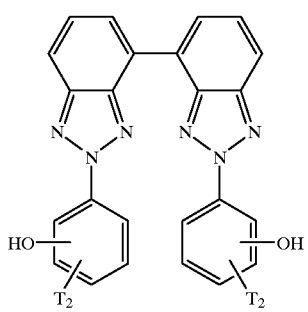

in which $T_2$ is hydrogen; or $C_1$–$C_{12}$alkyl, preferably iso-octyl.

A still further preferred class of triazole micronised organic UV absorbers is that having the formula (27)

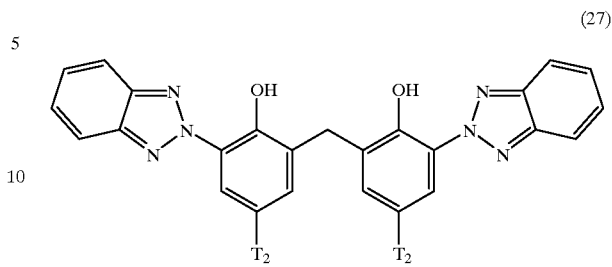

in which $T_2$ is $C_1$–$C_{12}$alkyl, preferably iso-octyl.

A preferred class of vinyl group-containing amide micronised organic UV absorbers is that having the formula $$R_7-(Y)_m-CO-C(R_8)=C(R_9)-N(R_{10})(R_{11}) \quad (28)$$

in which $R_7$ is $C_1$–$C_3$alkyl, preferably $C_1$–$C_2$alkyl, or phenyl optionally substituted by one, two or three substituents selected from OH, $C_1$–$C_3$alkyl, $C_1$–$C_3$alkoxy or CO—$OR_4$ in which $R_4$ has its previous significance; $R_8$, $R_9$, $R_{10}$ and $R_{11}$ are the same or different and each is $C_1$–$C_3$alkyl, preferably $C_1$–$C_2$alkyl, or hydrogen; Y is N or O; and m has its previous significance.

Preferred compounds of formula (28) are 4-methyl-3-penten-2-one, ethyl-3-methylamino-2-butenoate, 3-methylamino-1-phenyl-2-buten-1-one and 3-methylamino-1-phenyl-2-buten-1-one.

A preferred class of cinnamic acid amide micronised organic UV absorbers is that having the formula (29)

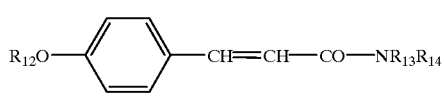

in which $R_{12}$ is hydroxy or $C_1$–$C_4$alkoxy, preferably methoxy or ethoxy; $R_{13}$ is hydrogen or $C_1$–$C_4$alkyl, preferably methyl or ethyl; and $R_{14}$ is —(CONH)$_m$-phenyl in which m has its previous significance and the phenyl group is optionally substituted by one, two or three substituents selected from OH, $C_1$–$C_3$alkyl, $C_1$–$C_3$alkoxy or CO—$OR_4$ in which $R_4$ has its previous significance. Preferably $R_{14}$ is phenyl, 4-methoxyphenyl or the phenylaminocarbonyl group.

A preferred class of sulfonated benzimidazole micronised organic UV absorbers is that having the formula (30)

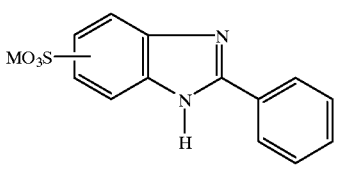

in which M is hydrogen or an alkali metal, preferably sodium, an alkaline earth metal, such as magnesium or calcium, or zinc.

In the compounds of formula (1) to (30), $C_1$–$C_{12}$alkyl groups may be methyl, ethyl, n-propyl or isopropyl, butyl, pentyl, amyl, isoamyl, hexyl, heptyl, octyl, iso-octyl, nonyl, decyl, undecyl oder dodecyl, methyl being preferred; and $C_1$–$C_3$ alkoxy groups include methoxy, ethoxy, propoxy and isopropoxy, methoxy and ethoxy being preferred.

$C_2$–$C_4$ carboxyalkyl includes carboxymethyl, carboxyethyl, carboxypropyl and carboxyisopropyl, carboxymethyl being preferred.

$C_5$–$C_8$ cycloalkyl includes cyclopentyl, cyclohexyl and cyclooctyl.

The compounds of formula (1) to (30) are known. The compounds of formula (24) are described, together with their production, in U.S. Pat. No. 4,617,390.

Preferably, the micronised organic UV absorber, component a) of the new sun protection agent, has a mean particle size in the range of from 0.01 to 2, more preferably from 0.02 to 1.5, especially from 0.05 to 1.0$\mu$.

The oil-soluble organic UV absorber, the optional component b) of the sun protection agent of the present invention, may be any known oil-soluble organic UV absorber, especially those which are already approved and marketed for cosmetic use. Such oil-soluble organic UV absorbers are described, for instance, in "Sunscreens", Development, Evaluation and Regulatory Aspects, Eds.: N. J. Lowe and N. A. Shaath, M. Dekker Inc., New York and Basel, 1990; and Ken Klein, Encyclopedia of UV absorbers for sunscreen products, Cosmetics & Toiletries 107 45–64 (1992).

The oil-soluble, non-micronised UV absorber may be, for example, a p-aminobenzoic acid derivative such as an ester, salt or an amine-modified derivative of p-aminobenzoic acid; a salicylic acid derivative such as an ester or salt thereof; a benzophenone derivative; a dibenzoylmethane derivative; a diphenylacrylate derivative; a benzofuran derivative; a polymeric UV absorber containing one or more silico-organic residues; a cinnamate ester; a camphor derivative; a trianilino-s-triazine derivative; phenylbenzimidazole sulfonic acid and its salts; urocanic acid (3-imidazol-4-yl-acrylic acid) or its ethyl ester; menthyl anthranilate; a benzotriazole; a hydroxyphenyltriazine derivative; or a bis-resorcinol-dialkylaminotriazine.

Specific examples of a p-aminobenzoic acid derivative include 4-aminobenzoic acid (PABA), ethyl dihydroxypropyl PABA having the formula

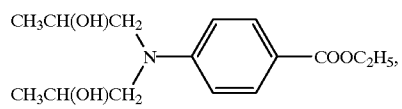

PEG-25 PABA having the formula

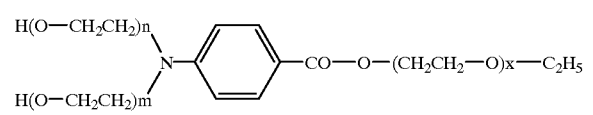

in which m, n and x are the same and each is approximately 25, octyl dimethyl PABA having the formula:

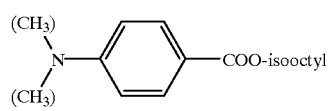

and glyceryl aminobenzoate having the formula

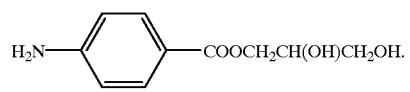

Specific examples of a salicylic acid derivative include homosalate (homomenthyl salicylate) having the formula

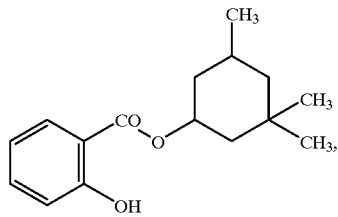

triethanolamine salicylate having the formula

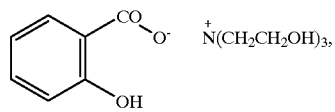

amyl p-dimethylamino benzoate having the formula

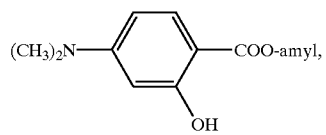

octyl salicylate having the formula

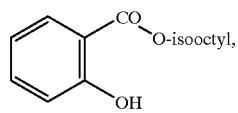

4-isopropylbenzylsalicylate having the formula

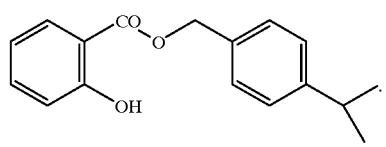

Specific examples of benzophenone derivatives include benzophenone-3-(2-hydroxy-4-methoxybenzophenone), benzophenone-4 (2-hydroxy-4-methoxybenzophenone-5-sulfonic acid) and benzophenone-8-(2,2'-dihydroxy-4-methoxybenzophenone).

A specific example of a dibenzoylmethane derivative is butyl methoxydibenzoylmethane [1-(4-tert.-butyl)-3-(4-methoxyphenyl)propane-1,3-dione].

Specific examples of a diphenylacrylate derivative include octocrylene (2-ethylhexyl-2-cyano-3,3'-diphenyl acrylate) and etocrylene (ethyl-2-cyano-3,3'-diphenyl acrylate).

Specific examples of a benzofuran derivative include the 3-(benzofuranyl)-2-cyanoacrylates described in U.S. Pat. No. 5,338,539 or EP 582189, especially the compounds having the formula

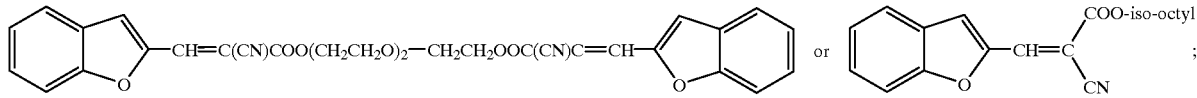

the 2-(2-benzofuranyl)-5-tert.-butylbenzoxazoles described in U.S. Pat. No. 5,518,713 and the 2-(p-aminophenyl) benzofurans described in U.S. Pat. No. 5,362,481.

Specific examples of a polymeric UV absorber containing one or more silico-organic residues are the benzylidenemalonate silicone derivatives disclosed in EP 709080, in particular the compound having the formula:

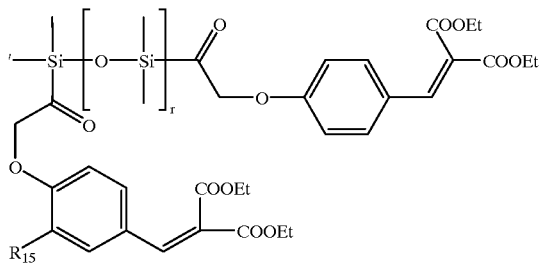

in which $R_{15}$ is H or OMe and r is approximately 7; and the polymers of the benzotriazole silicone type described in WO 94/06404, in particular the compound having the formula:

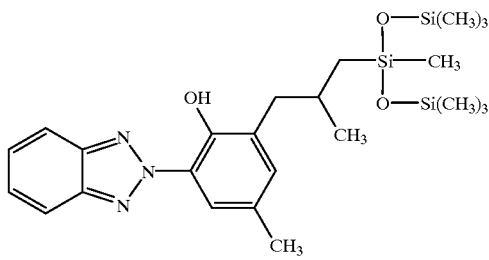

Specific examples of a cinnamate ester include octyl methoxy cinnamate (4-methoxycinnamic acid 2-ethylhexyl ester), diethanolamine methoxy cinnamate (diethanolamine salt of 4-methoxycinnamic acid), isoamyl p-methoxycinnamate (4-methoxycinnamic acid 2-isoamyl ester), 2,5-diisopropyl methyl cinnamate, the cinnamido derivatives disclosed in U.S. Pat. No. 5,601,811 and the derivatives described in WO 97/00851.

Specific examples of camphor derivatives are 4-methylbenzylidene camphor [3-(4'-methyl)benzylidene-bornan-2-one], 3-benzylidene camphor (3-benzylidene-bornan-2-one), polyacrylamidomethyl benzylidene camphor {N-[2 (and 4)-2-oxyborn-3-yliden-methyl)benzyl]acrylamide polymer}, trimonium benzylidene camphor sulfate [3-(4'-trimethylammonium)-benzylidene-bornan-2-one methyl sulfate], terephthalydene dicamphor sulfonic acid {3,3'-(1,4-phenylenedimethine)-bis-(7,7-dimethyl-2-oxo-bicyclo-[2.2.1]heptan-1-methanesulfonic acid} and salts thereof and benzylidene camphor sulfonic acid [3-(4'-sulfo) benzylidene-bornan-2-one] and salts thereof.

Specific examples of trianilino-s-triazine derivatives include octyl triazine [2,4,6-trianilino-(p-carbo-2'-ethyl-1'-oxy)-1,3,5-triazine, the trianilino-s-triazine derivatives disclosed in U.S. Pat. No. 5,332,568, the trianilino-s-triazine derivatives described in EP 517104, trianilino-s-triazine derivatives disclosed in EP 570838, the trianilino-s-triazine derivatives described in U.S. Pat. No. 5,252,323, the trianilino-s-triazine derivatives described in WO 93/17002-A1 and the trianilino-s-triazine derivatives disclosed in WO 97/03642-A1.

A specific example of a benzotriazole is 2-(2-hydroxy-5-methyl-phenyl)benzotriazole.

Specific examples of hydroxyphenyltriazine derivatives include, e.g. those described EP-A1-775,698, such as 2,4-bis-{[4—(2-ethyl-hexyloxy)-2-hydroxy]-phenyl}-6-(4-methoxyphenyl) -1,3,5-triazine.

Specific examples of bis-resorcinol-dialkylaminotriazines are, e.g., those described in EP-A1-780,382.

The inorganic micropigment UV absorber, the optional component b) of the new sun protection agent may be, for example, titanium dioxide coated with aluminium oxide or silicon dioxide, zinc oxide coated with aluminium oxide or silicon dioxide, or mica.

The polymeric hollow sphere component, component c) of the new sun protection agent according to the present invention, may be, for instance, those described in EP-A-761,201.

The polymeric hollow sphere component is preferably a commercially available styrene/acrylic acid copolymer hollow sphere material. The styrene/acrylic acid copolymer is supplied as an aqueous dispersion comprising styrene/acrylic acid copolymer beads having a particle size below 1 micron. The said aqueous dispersion preferably has a solids content within the range of from 20 to 50%, more preferably from 25 to 45%, by weight; a voids volume of 15 to 60%, more preferably from 20 to 55%; a mean particle size of 0.1 to 5 microns, more preferably 0.1 to 1.5 microns; and a wall thickness of 0.01 to 1 micron, more preferably from 0.02 to 0.5 micron.

The polymeric hollow sphere component may, of course, be derived from any suitable monomer and need not be limited to styrene/acrylic acid copolymer hollow sphere material.

Suitable hollow sphere material are for example acrylonitrile copolymers, like copolymers of acrylonitrile with acrylic acid, methacrylic acid, styrene or vinylidene chloride.

Preferred polymeric hollow sphere components are those which are substantially insoluble in cosmetic formulation components for sunscreens, since unduly high solubility therein can lead to an undesired decrease in the UV-protection performance of the resulting sunscreen formulation.

The present invention also provides a sunscreen composition comprising A) 0.1 to 15%, preferably 0.5 to 10% by weight, based on the total composition of a sun screen agent according to the present-invention; and B) a cosmetically acceptable carrier.

The sunscreen composition of the present invention may be produced by physically blending the sun screen agent according to the present invention and a cosmetically acceptable carrier by any conventional method, e.g. by simply stirring the two materials together.

The sunscreen composition of the invention may be formulated as a water-in oil or an oil-in-water dispersion, an oil or oil-alcohol lotion, a vesicular dispersion of an ionic or nonionic amphiphilic lipid, a gel, a solid stick or an aerosol formulation.

When formulated as a water-in oil or an oil-in-water dispersion, the cosmetically acceptable carrier preferably comprises 5 to 50% of an oil phase, 5 to 20% of an emulsifier and 30 to 90% of water, each by weight based on the total weight of the carrier.

The oil phase may comprise any oil conventionally used in cosmetic formulations, especially an emollient e.g., one or more of a fatty alcohol; hydrocarbon oil; a natural or synthetic triglyceride; a wax including esters of long-chain acids and alcohols as well as compounds having wax-like properties; a silicone oil; a fatty acid ester or a fatty alcohol; and lanoline-containing products.

Examples of fatty alcohols include cetyl alcohol, stearyl alcohol, octyidodecanol, cetearyl alcohol and oleyl alcohol; examples of hydrocarbon oils are, e.g., mineral oil (light or heavy), petrolatum (yellow or white), polyethylene, paraffin, squalane, microcrystalline wax, ceresin, polybutene and hydrogenated polyisobutene; examples of a natural or synthetic triglyceride include castor oil, caprylic/capric triglyceride, Japan wax, hydrogenated vegetable oil, sweet almond oil, wheat germ oil, sesame oil, hydrogenated cottonseed oil, coconut oil, wheat germ glycerides, avocado oil, corn oil, trilaurin, hydrogenated castor oil, shea butter, cocoa butter, soybean oil, mink oil, sunflower oil, safflower oil, macadarnia nut oil, olive oil, hydrogenated tallow, apricot kernel oil, hazelnut oil and borage oil; examples of a wax including esters of long-chain acids and alcohols as well as compounds having wax-like properties are, e.g., carnauba wax, beeswax (white or yellow), lanolin, candelellila wax, ozokerite, lanolin oil, paraffin, Japan wax, microcrystalline wax, ceresin, jojoba oil, cetayl esters wax, synthetic jojoba oil, synthetic beeswax and lanolin wax; a silicone oil is e.g. dimethicone or cyclomethicone; examples of a fatty acid ester or a fatty alcohol include isopropyl myristate, isopropyl palmitate, octyl palmitate, isopropyl lanolate, acetylated lanolin alcohol, the benzoate of $C_{12}$–$C_{15}$alcohols, cetearyl octanoate, cetyl palmitate, myristyl myristate, myristyl lactate, cetyl acetate, propylene glycol dicaprylate/caprate, decyl oleate, acetylated lanolin, stearyl heptanoate, diisostearyl malate, octyl hydroxystearate, octyl hydroxystearate and isopropyl isostearate; and examples of lanoline-containing products include lanolin, lanolin oil, isopropyl lanolate, acetylated lanolin alcohol, acetylated lanolin, hydroxylated lanolin, hydrogenated lanolin and lanolin wax.

The emulsifier may comprise any emulsifier conventionally used in cosmetic formulations, e.g., one or more of an ethoxylated ester of a natural oil derivative such as a polyethoxylated ester of hydrogenated castor oil; a silicone oil emulsifier such as a silicone polyol; an optionally ethoxylated fatty acid soap; an ethoxylated fatty alcohol; an optionally ethoxylated sorbitan ester; an ethoxylated fatty acid; or an ethoxylated glyceride.

The sunscreen composition of the invention may also comprise further components which are known to perform a useful function in a sunscreen composition. Examples of such further components include, e.g., emollients, skin moisturisers, skin tanning accelerators, antioxidants, emulsion stabilisers, thickening agents such as xanthan, moisture-retention agents such as glycerine, film formers, preservatives, perfumes and colourants.

The sunscreen composition of the invention provides excellent protection of the human against the damaging effects of sunlight, while permitting safe tanning of the skin. Moreover, the sunscreen composition of the invention has a skin waterproofing effect.

The following Examples further illustrate the present invention. Parts and percentages shown therein are by weight unless otherwise stated.

EXAMPLES 1 to 10

The aqueous dispersions of styrene/acrylic acid copolymer hollow spheres used in the following test methods have the following physical characteristics:

| Polymer | solids content (%) | voids volume (%) | mean particle size (microns) | wall thickness (microns) |
|---|---|---|---|---|
| Ropaque HP-91 (I*) | 27.5 | 50 | 1.0 | 0.1 |
| Ropaque OP-84-2M (II*) | 40.0 | 22 | 0.5 | 0.1 |
| Ropaque OP-90 E (III*) | 37.5 | 33 | 0.4 | 0.06 |

The basic recipe used was the following oil-in-water cream:
A) oil phase composition:

| | |
|---|---|
| Tegin P | 1.0% |
| Thickly viscous paraffin oil | 5.0% |
| Stearic acid | 1.5% |
| Lanette O | 0.4% |
| Propyl paraben | 0.1% |
| Oil-soluble UVA (Parsol MCX) | x%. |

Parsol MCX is octyl methoxycinnamate.
B) aqueous phase composition:

| | |
|---|---|
| Water | 84.3% |
| Triethanolamine | 0.8% |
| Glycerine (85%) | 4.0% |
| Carbopol 934P | 0.1% |
| Methyl paraben | 0.1% |
| Aqueous micronised UVA (compound of formula (101)) | y% |
| Polymer | z% |

Compound of formula (101) is 2,2'-methylene-bis-[6-(2H-benzotriazole-2-yl)-4-(1,1,3,3-tetramethylbutyl)-phenol]:

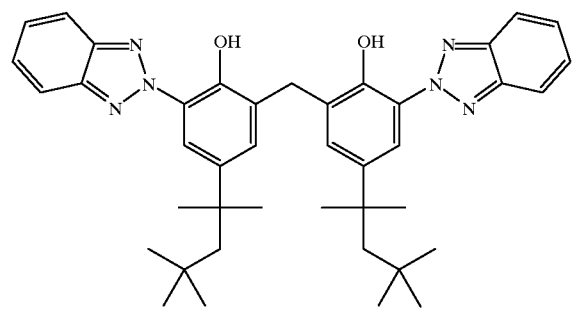

The individual test formulations are produced as follows. The oil-soluble UVA (Parsol MCX) is dissolved in a specified amount (see following Table) in the oil phase. The aqueous micronised UVA (compound of formula (101)), optionally together with the polymer, is incorporated into the aqueous phase. The two phases are separately heated to 75° C. and then the oil phase is slowly stirred into the water phase and the whole mixture is stirred cold.

The individual test formulations so obtained are then evaluated, in vitro, for their SPF performance using an SPF-290 analyser (Fa. Optometrics). Four brush strokes of each test formulation are applied, in a layer thickness of 2 $\mu$l/cm$^2$ on to Transpore film (3M) and 9 SPF measurements are conducted from each applied brush stroke. The SPF values obtained are shown in the following Table 1, together with the mean values and standard deviations, for each of the individual 36 measurements. The percentage amounts of of polymer shown in the Table 1 are based on the weight of active substance.

TABLE 1

| Example | x% | y% | Polymer (I*) % | Polymer (II*) % | Polymer (III*) % | SPF |
|---|---|---|---|---|---|---|
| (control) | — | — | — | — | — | 1.2 ± 0 |
| 1 | Parsol MCX 2.7% | comp. (101) 5% | | | | 17.8 ± 1.9 |
| 2 | Parsol MCX 2.7% | — | 2.5% | | | 7.9 ± 0.6 |
| 3 | Parsol MCX 2.7% | — | | 2.5% | | 8.2 ± 0.9 |
| 4 | Parsol MCX 2.7% | — | | | 2.5% | 8.1 ± 0.9 |
| 5 | — | comp. (101) 5% | 2.5% | | | 11.9 ± 1.8 |
| 6 | — | comp. (101) 5% | | 2.5% | | 8.9 ± 0.8 |
| 7 | — | comp. (101) 5% | | | 2.5% | 8.5 ± 1.0 |
| 8 | Parsol MCX 2.7% | comp. (101) 5% | 2.5% | | | 20.1 ± 1.7 |
| 9 | Parsol MCX 2.7% | comp. (101) 5% | | 2.5% | | 23.1 ± 1.1 |
| 10 | Parsol MCX 2.7% | comp. (101) 5% | | | 2.5% | 23.0 ± 3.1 |

The results in Table 1 show that the basic formulation (with no UV absorber) offers no UV protection. Parsol MCX and micronised compound (101), when used together, demonstrate a synergistic UV protection. Compound (101) and the polymer spheres, when used together, demonstrate an improved UV protection. The three-component combination of Parsol MCX, micronised compound (101) and the polymer spheres, when used together, demonstrate an outstanding synergistic UV protection.

The results in the Table also show that the cosmetic producer, by the use of relatively cheap polymer spheres, is able to formulate high SPF sun protection formulations using relatively small amounts of expensive UV absorbers.

EXAMPLES 11 to 13

Using the same formulations as described in Examples 1 to 10, but varying the relative proportions of the polymer spheres, the following further results are obtained. The percentage amounts of of polymer shown in Table 2 are based on the weight of active substance.

TABLE 2

| Example | x % | y % | Polymer (III*) % | SPF |
|---|---|---|---|---|
| -(control) | — | — | — | 1.2 |
| 11 | Parsol MCX 2.7% | compound (101) 5% | 5.0% | 28.5 |
| 12 | Parsol MCX 2.7% | compound (101) 5% | 7.5% | 58.5 |
| 13 | Parsol MCX 2.7% | compound (101) 5% | 10.0% | 47.5 |

EXAMPLES 14 and 15

The following basic oil-in-water formulation is made up:

| Oil Phase 1 | |
|---|---|
| propylene glycol stearate | 1.0% |
| mineral oil | 5.0% |
| stearic acid | 1.5% |
| cetearyl alcohol | 0.4% |
| propylparaben | 0.1% |
| test oil-soluble UV absorber | 2.7% |
| Aqueous Phase 2 | |
| triethanolamine | 0.8% |
| glycerine (85%) | 4.0% |
| carbomer | 0.1% |
| methylparaben | 0.1% |
| water | to 100%. |

Inorganic micropigment (micro-TiO$_2$, silicon-coated) is incorporated (6.0% by weight based on the solids content of the total formulation) into the oil phase. Micronised test organic UV absorber is incorporated (6.0% by weight based on the solids content of the total formulation), as a suspension, into the aqueous phase.

Phases 1 and 2 are separately heated to 75° C. With continuous stirring, the oil phase is added to the aqueous phase and, while homogenising, the mixture is cooled to 30° C.

The individual test formulations so obtained are then evaluated, in vitro, for their SPF performance using the COLIPA standard. The SPF values obtained are shown in the following Table 3:

TABLE 3

| Example | Test oil-soluble UVA (% by weight) | Test micronised UVA (% by weight) | SPF in vitro |
|---|---|---|---|
| — | 2.7% UVA I | — | 4.2 |
| — | — | 6.0% by weight UVA II | 7.7 |
| — | — | 6.0% by weight silicon-coated TiO$_2$ | 4.8 |
| 14 | 2.7% UVA I | 6.0% by weight UVA II | 14.2 |
| 15 | 2.7% UVA I | 6.0% by weight silicon-coated TiO$_2$ | 7.9 |

UVA I is 2-ethylhexyl-p-methoxycinnamate and UVA II is a 25% aqueous dispersion of [2-(2-hydroxy-4-methoxyphenyl)-4,6-diphenyl-1,3,5-triazine] having a mean particle size of 0.55 micron.

The results in Table 3 demonstrate that the two component sun screen agents according to the present invention exhibit unexpected synergistic SPF effects, the results in Example 14 being particularly outstanding.

EXAMPLES 16 and 17

Using the base oil-in-water formulation of Examples 14 and 15, various oil-soluble UVAs and micronised UVAs are incorporated in specific amounts. The respective formulations are then examined for their in vitro SPF performance using an SPF-analyser 290 (Optometrics). The evaluations are conducted using the method of Diffey & Robson (J. Soc. Cosmet. 40 127–133, 1989).

The results are set out in the following Table 4:

TABLE 4

| Example | Oil-soluble UVA | Micronised UVA | SPF |
|---|---|---|---|
| — | — | 6.4% by weight UVA III | 5.4 |
| 16 | 4.0% by weight UVA I | 6.4% by weight UVA III | 22.7 |
| 17 | 4.0% by weight UVA IV | 6.4% by weight UVA III | 16.7 |

UVA III is a 50% aqueous dispersion of [2,2'-methylene-bis-6(2H-benzotriazole-2-yl)-4-(1,1,3,3-tetramethylbutyl)-phenol] having a mean particle size of 0.25 micron. UVA IV is 4-methyl-benzylidene camphor.

The results in Table 5 show that the two component sun screen agents according to the present invention exhibit unexpected synergistic SPF effects.

EXAMPLES 18 and 19

A pre-dispersion A is produced consisting of a 50% aqueous dispersion of micronised UVA III.

There are then added to pre-dispersion A, 2% of xanthan gum and 0.4% propylene glycol, to produce pre-dispersion B1. There are then added to pre-dispersion B1, 2.0% of polyvinylpyrrolidone (MW 8000) to produce pre-dispersion B2. The pre-dispersions A, B1 and B2 are then incorporated into separate samples of the same simple oil-in-water formulation and the final formulations are used for in vitro SPF determinations employing an SPF-analyser 290 (Optometrics). The evaluations are conducted using the method of Diffey & Robson (J. Soc. Cosmet. 40 127–133, 1989).

The results are set out in the following Table 5:

TABLE 5

| Example | Test formulation | SPF |
|---|---|---|
| — | Final formulation with pre-dispersion A | 11.7 |
| 18 | Final formulation with pre-dispersion B1 | 18.0 |
| 19 | Final formulation with pre-dispersion B2 | 21.1 |

The results in Table 5 show that the two component sun screen agents according to the present invention exhibit unexpected improved SPF effects.

EXAMPLES 20 to 25

The following basic oil-in-water formulation is made up:

| Phase 1 | |
|---|---|
| cetearyl alcohol; PEG-40; Castor oil; sodium cetearyl sulfate mixt. | 3.15% |
| decyl oleat | 15.0% |
| test oil-soluble UVA IV or V | 4.0% |
| propylparaben | 0.1% |
| Phase 2 | |
| 50% aqueous dispersion of micronised UVA III | 6 or 12% |
| methylparaben | 0.3% |
| disodium EDTA | 0.1% |
| water | 50.75 or 45.75% |
| Phase 3 | |
| carbomer (Carbopol 934P) | 0.3% |
| sodium hydroxide (45%) | 0.3% |
| water | 20% |

Phase 1 is heated to 75–80° C. Phase 2 is heated to 80° C. while applying thorough homogenisation. Phase 1 is then added to phase 2, while applying continuous stirring. Phase 3 is then added to the mixture of phases 1 and 2, while applying continuous stirring, and then re-homogenised for 3 minutes. After replenishing water loss, the whole mixture is homogenised until it is cool.

The individual test formulations so obtained are then evaluated, in vitro, for their SPF performance using an SPF-290 analyser (Fa. Optometrics). Four brush strokes of each test formulation are applied, in a layer thickness of 2 $\mu$l/cm$^2$ on to Transpore film (3M) and 9 SPF measurements are conducted from each applied brush stroke. The SPF values obtained are shown in the following Table 7, together with the mean values and standard deviations, for each of the individual 36 measurements.

TABLE 6

| Example | Oil-soluble UVA | Micronised UVA in a 50% suspension | SPF |
|---|---|---|---|
| 20 | 4% UVA V | 6% UVA III | 16.3 ± 4.1 |
| 21 | 4% UVA V | 12% UVA III | 31.4 ± 9.4 |
| 22 | 4% UVA VI | 6% UVA III | 16.0 ± 4.0 |
| 23 | 4% UVA VI | 12% UVA III | 30.6 ± 9.2 |
| 24 | 4% UVA VII | 6% UVA III | 25.3 ± 7.6 |
| 25 | 4% UVA VII | 12% UVA III | 48.2 ± 14.5 |

UVA V is octyl-methoxycinnamate; UVA VI is 3-(4-methylbenzidene)-bornan-2-one; and UVA VII is 2,4,6-trianilino-p-(carbo-2'-ethylhexyl-1'-oxy)-1,3,5-triazine.

EXAMPLE 26

The following basic oil-in-water formulation is made up:

| Oil Phase | |
|---|---|
| isostearyl isostearate | 4.0% |
| caprylic/capric triglyceride | 4.0% |
| liquid paraffin | 3.3% |
| stearyl alcohol | 1.4% |
| cetyl alcohol | 1.4% |
| titanium dioxide (Eusolex T-2000) | 4.0% |
| dimethicone | 1.0% |
| propylparaben | 0.1% |
| Aqueous Phase | |
| sodium chitosan methylene phosphonate | 0.01% |
| sodium cetearyl sulfate | 0.5% |
| methylparaben | 0.1% |
| compound (26) (50%) | 6.0% |
| water | to 100%. |

The two phases are separately heated to 65° C. and then the oil phase is stirred into the aqueous phase and the whole mixture is stirred cold. The pH of the emulsion so obtained is adjusted to 6.5 to 7.0 and then the emulsion is evaluated, in vitro, to determine its SPF performance, using an SPF-290 analyser (Fa. Optometrics). The SPF value obtained is 21. When the experiment is repeated, but omitting the compound (26) from the aqueous phase, the SPF value is only 9.

What is claimed is:

1. A sun protection agent comprising
   a) a micronised organic UV absorber;
   b) an oil-soluble, non-micronised UV absorber selected from the group consisting of p-aminobenzoic acid derivatives, salicylic acid derivatives, benzophenone derivatives, dibenzoylmethane derivatives, diphenylacrylate derivatives, benzofuran derivatives, polymeric UV absorbers containing one or more silico-organic residues, cinnamate esters, camphor derivatives, trianilino-s-triazine derivatives, urocanic acid (3-imidazol-4-yl-acrylic acid) or its ethyl ester, menthyl anthranilate, benzotriazoles and hydroxyphenyltriazine derivatives; and c) a styrene/acrylic acid copolymer hollow sphere material.

2. A sun protection agent according to claim 1 in which the relative proportions of components a):b) and/or c) ranges from 20:80 to 80:20.

3. A sun protection agent according to claim 1 in which the micronised organic UV absorber is a triazine, a benzotriazole, a vinyl group-containing amide, a cinnamic acid amide or a sulfonated benzimidazole UV absorber.

4. A sun protection agent according to claim 3 in which the triazine UV absorber has the formula:

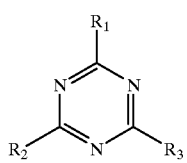

(1)

in which $R_1$, $R_2$ and $R_3$, independently, are H, OH, $C_1$–$C_3$alkoxy, $NH_2$, NH—$R_4$ or $N(R_4)_2$ in which $R_4$ is $C_1$–$C_3$alkyl, $OR_4$ in which $R_4$ has its previous significance, phenyl, phenoxy or anilino, or pyrrolo, in which the respective phenyl, phenoxy or anilino, or pyrrolo moieties are optionally substituted by one, two or three substitutents selected from OH, carboxy, CO—$NH_2$, $C_1$–$C_3$alkyl or -alkoxy, $C_2$–$C_4$ carboxyalkyl, $C_5$–$C_8$cycloalkyl, a methylidenecamphor group, a group —(CH=CH)$_m$C(=O)—$OR_4$ in which m is 0 or 1 and $R_4$ has its previous significance, or a group

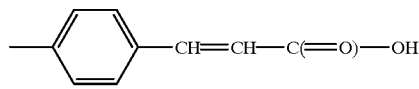

or the corresponding alkali metal, ammonium, mono-, di- or tri-$C_1$–$C_4$alkylammonium, mono-, di- or tri-$C_2$–$C_4$alkanolammonium salts, or the $C_1$–$C_3$alkyl esters thereof.

5. A sun protection agent according to claim 4 in which the triazine compound has the formula

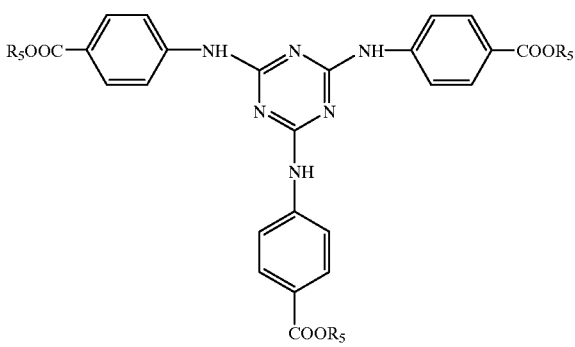

in which the individual radicals $R_5$ are the same or different and each is hydrogen; an alkali metal; an ammonium group $N(R_6)_4$ in which $R_6$ is hydrogen or an organic radical; $C_1$–$C_3$alkyl; or a polyoxyethylene radical which contains from 1 to 10 ethylene oxide units and the terminal OH group of which may be etherified by a $C_1$–$C_3$alcohol.

6. A sun protection agent according to claim 3 in which the triazole organic UV absorber has the formula:

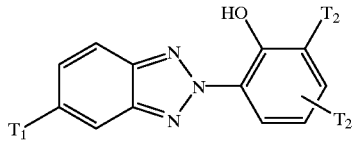

in which $T_1$ is $C_1$–$C_3$alkyl or hydrogen; and $T_2$ is $C_1$–$C_4$alkyl, optionally substituted by phenyl.

7. A sun protection agent according to claim 3 in which the triazole organic UV absorber has the formula:

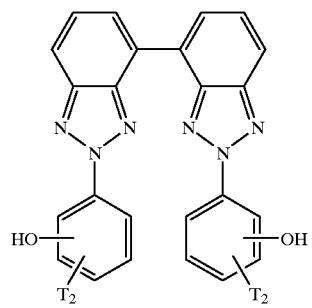

in which $T_2$ is hydrogen or $C_1$–$C_{12}$alkyl.

8. A sun protection agent according to claim 7 wherein $T_2$ is iso-octyl.

9. A sun protection agent according to claim 3 in which the benzotriazole organic UV absorber has the formula:

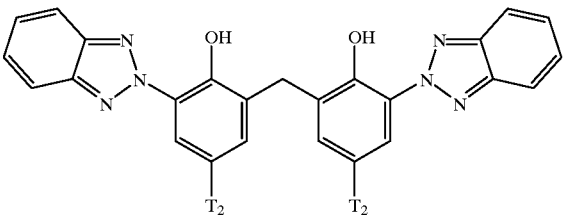

in which $T_2$ is hydrogen or $C_1$–$C_{12}$alkyl.

10. A sun protection agent according to claim 3 in which the vinyl group-containing amide organic UV absorber has the formula:

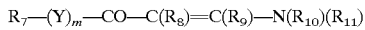

$R_7$—(Y)$_m$—CO—C($R_8$)=C($R_9$)—N($R_{10}$)($R_{11}$)

in which $R_7$ is $C_1$–$C_3$alkyl or phenyl optionally substituted by one, two or three substituents selected from OH, $C_1$–$C_3$alkyl, $C_1$–$C_3$alkoxy or CO—$OR_4$ in which $R_4$ is $C_1$–$C_3$alkyl, $OR_4$ in which $R_4$ has its previous significance, phenyl, phenoxly anilino, or pyrrolo, in which the respective phenyl, phenoxy or anilino, or pyrrolo moieties are optionally substituted by one, two or three substituents selected from OH, carboxy, CO—$NH_2$, $C_1$–$C_3$alkyl or -alkoxy, $C_2$–$C_4$carboxyalkyl, $C_5$–$C_8$cycloalkyl, a methylidenecamphor group, a group —C(CH=CH)$_m$C(=O)—$OR_4$ in which m is 0 or 1 and $R_4$ has its previous significance, or a group

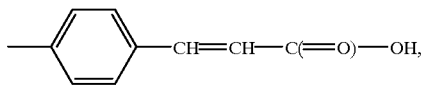

or the corresponding alkali metal, ammonium, mono-, di- or tri-$C_1$-$C_4$ alkylammonium, mono-, di- or tri-$C_2$-$C_4$ alkanolammonium salts, or the $C_1$-$C_3$ alkyl esters thereof; $R_8$, $R_9$, $R_{10}$ and $R_{11}$ are the same or different and each is $C_1$-$C_3$ alkyl or hydrogen, and Y is N or O.

11. A sun protection agent according to claim 3 in which the cinnamic acid amide organic UV absorber has the formula:

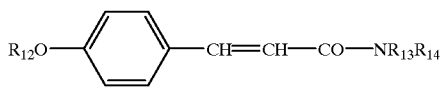

in which $R_{12}$ is hydroxy or $C_1$-$C_4$ alkoxy; $R_{13}$ is hydrogen or $C_1$-$C_4$ alkyl; and $R_{14}$ is —(CONH)$_m$-phenyl in which m is 0 or 1 and the phenyl group is optionally substituted by one, two or three substituents selected from OH, $C_1$-$C_3$ alkyl, $C_1$-$C_3$ alkoxy or CO—OR$_4$ in which $R_4$ is $C_1$-$C_3$ alkyl, OR$_4$ in which $R_4$ has its previous significance, phenyl, phenoxy anilino, or pyrrolo, in which the respective phenyl, phenoxy or anilino, or pyrrolo moieties are optionally substituted by one, two or three substitutents selected from OH, carboxy, CO—NH$_2$, $C_1$-$C_3$ alkyl or -alkoxy, $C_2$-$C_4$-carboxyalkyl, $C_5$-$C_8$ cycloalkyl, a methylidenecamphor group, a group —(CH=CH)$_m$C(=O)—OR$_4$ in which m is 0 or 1 and $R_4$ has its previous significance, or a group

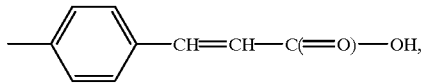

or the corresponding alkali metal, ammonium, mono-, di- or tri-$C_1$-$C_4$ alkylammonium, mono-, di- or tri-$C_2$-$C_4$ alkanolammonium salts, or the $C_1$-$C_3$ alkyl esters thereof.

12. A sun protection agent according to claim 3 in which the sulfonated benzimidazole organic UV absorber has the formula:

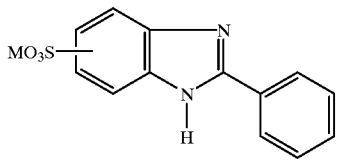

in which M is hydrogen or an alkali metal, an alkaline earth metal or zinc.

13. A sun protection agent according to claim 1 in which the micronised organic UV absorber, component a), has a mean particle size in the range of from 0.01 to 2μ.

14. A sun protection agent according to claim 1 in which the cinnamate ester is octyl methoxy cinnamate (4-methoxycinnamic acid 2-ethylhexyl ester), diethanolamine methoxy cinnamate (diethanolamine salt of 4-methoxycinnamic acid), isoamyl p-methoxycinnamate (4-methoxycinnamic acid 2-isoamyl ester), 2,5-diisopropyl methyl cinnamate or a cinnamido derivative.

15. A sun protection agent according to claim 1 in which the styrene/acrylic acid copolymer is in the form of an aqueous dispersion comprising styrene/acrylic acid copolymer beads having a particle size below 5 micron.

16. A sun protection agent according to claim 15 in which the aqueous dispersion has a solids content within the range of from 20 to 50%, and the copolymer beads have a voids volume of 15 to 60%, a mean particle size of 0.1 to 5 microns and a wall thickness of 0.01 to 1 micron.

17. A sunscreen composition comprising A) 0.1 to 15% by weight of a sun protection agent according to claim 1; and B) a cosmetically acceptable carrier.

18. A composition according to claim 17 in which the micronised organic UV absorber, component a), has a mean particle size in the range of from 0.01 to 2.0μ.

19. A composition according to claim 17 in which the sun protection agent is used together with one or more further UV absorbers which are conventionally used in cosmetic compositions for the protection of human skin against UV radiation.

20. A sunscreen composition according to claim 17 which is formulated as a water-in oil or an oil-in-water dispersion, an oil or oil-alcohol lotion, a vesicular dispersion of an ionic or nonionic amphiphilic lipid, an oil-alcohol or alcohol gel, a solid stick or an aerosol formulation.

21. A sunscreen composition according to claim 20 which is formulated as a water-in oil or an oil-in-water dispersion and component B) comprises 5 to 50% of an oil phase, 5 to 20% of an emulsifier and 30 to 90% of water, each by weight based on the total weight of the carrier.

22. A sunscreen composition according to claim 21 in which the oil phase comprises an emollient selected from the grout consisting of one or more of fatty alcohols; hydrocarbon oils; natural or synthetic triglycerides; waxes which include esters of long-chain acids and alcohols as well as compounds having wax-like properties; silicone oils; fatty acid esters or fatty alcohols; and lanoline-containing products.

23. A sunscreen composition according to claim 17 in which the sunscreen composition also comprises one or more further components selected from the group consisting of further emollients, skin moisturisers, skin tanning accelerators, antioxidants, emulsion stabilisers, thickening agents, moisture retention agents, film formers, preservatives, perfumes and colourants.

24. A sun protection agent according to claim 1 wherein component b) as a hydroxyphenyltriazine derivative is a bis-resorcinol-dialkylaminotriazine derivative.

* * * * *